United States Patent
Pipas et al.

(10) Patent No.: US 6,168,929 B1
(45) Date of Patent: Jan. 2, 2001

(54) METHOD OF IDENTIFYING AGENTS THAT DISRUPT THE INTERACTION OF SV40 T ANTIGEN WITH DNAK HOMOLOGUES

(75) Inventors: James M. Pipas; Jeffrey L. Brodsky, both of Pittsburgh, PA (US)

(73) Assignee: University of Pittsburgh, Pittsburgh, PA (US)

(*) Notice: Under 35 U.S.C. 154(b), the term of this patent shall be extended for 0 days.

(21) Appl. No.: 09/014,438

(22) Filed: Jan. 27, 1998

Related U.S. Application Data

(60) Provisional application No. 60/036,289, filed on Jan. 27, 1997.

(51) Int. Cl.⁷ .............................. C12Q 1/44; C07K 14/025
(52) U.S. Cl. .............................. 435/19; 530/324; 530/350; 530/826
(58) Field of Search ................................. 435/195, 810, 435/19; 530/324, 350, 826

(56) References Cited

PUBLICATIONS

Cheetham et al. (1992) *Biochem. J.* 284:469.
Campbell et al. (1997) *Genes & Development* 11:1098.
Karzai et al. (1'996) *J. Biol. Chem.* 271:11236.
Minami et al. (1996) *J. Biol. Chem.* 271:19617.
Sawai et al. (1994) *Virus Research* 31:367.
Sheng et al. (1997) *J. Virol.* 71:9410.
Srinivasan et al. (1997) *Mol. Cell. Biol.* 17:4761.
Stubal et al. (1997) *Mol. Cell Biol.* 17:4979.
Stubdal et al. (1996) *J. Virol.* 70:2781.
Wall et al. (1994) J. Biol. Chem., vol. 269, pp. 5446–5451.*
Kelley et al. (1994) TIBS, vol. 19, pp. 277–278.*
Tsai et al. (Apr. 19, 1996) J. Biol. Chem., vol. 271, pp. 9347–9354.*

* cited by examiner

*Primary Examiner*—Elizabeth Slobodyansky
(74) *Attorney, Agent, or Firm*—Baker Botts LLP

(57) ABSTRACT

The present invention provides a method of identifying agents that interfere with the interaction of the J-domain of the SV40 large T antigen with a Dnak protein. In a preferred embodiment, the Dnak protein is mammalian hsc70 or yeast Ssa1p.

4 Claims, 8 Drawing Sheets

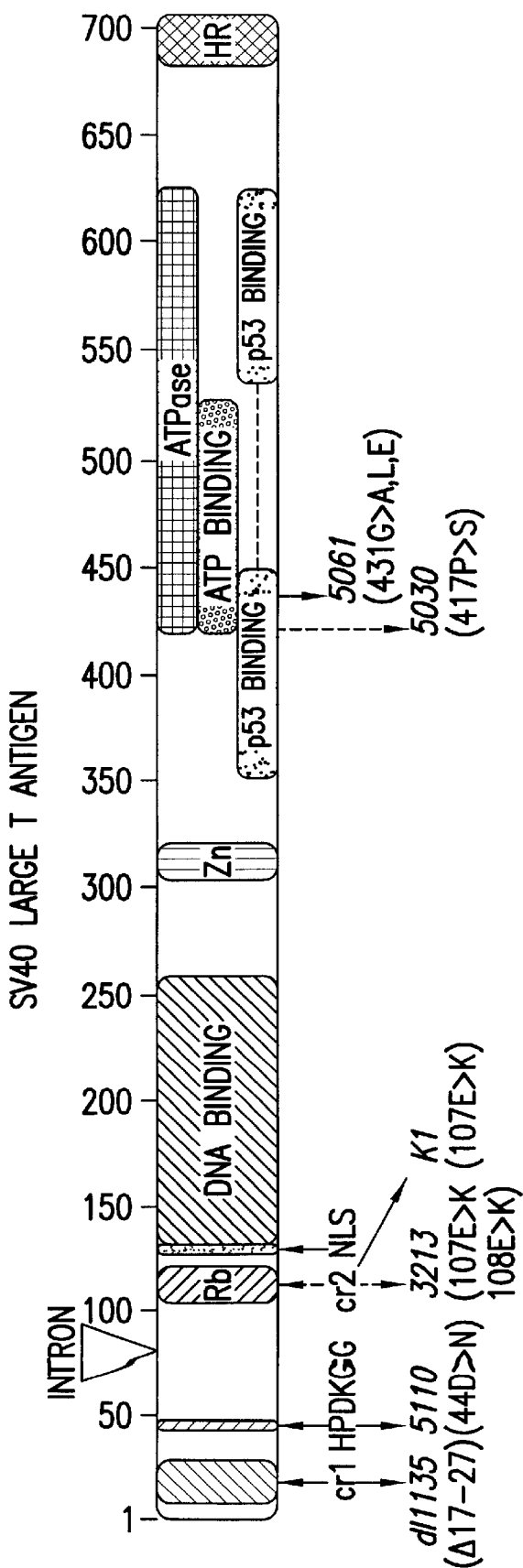
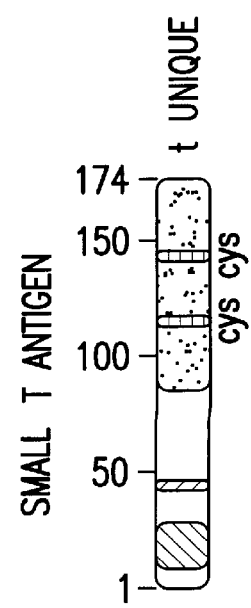
FIG. 1A
FIG. 1B

US 6,168,929 B1

METHOD OF IDENTIFYING AGENTS THAT DISRUPT THE INTERACTION OF SV40 T ANTIGEN WITH DNAK HOMOLOGUES

CROSS REFERENCE TO RELATED APPLICATION

This application claims the benefit of provisional application U.S. Ser. No. 60/036,289 filed on Jan. 27, 1997.

STATEMENT REGARDING FEDERALLY FUNDED RESEARCH

This invention was made with United States government support under grant numbers NIH/CA 40586 and NSF/MCB-9506002 awarded by the National Institutes of Health and the National Science Foundation, respectively. The United States government has certain rights in the invention.

BACKGROUND OF THE INVENTION

Simian virus 40 (SV40) encodes two proteins involved in tumorigenesis, the large and small tumor antigens. Large tumor antigen (T antigen) orchestrates many aspects of productive viral infection and is necessary, and in many cases sufficient, for tumorigenesis. T antigen is a 708 amino acid multifunctional protein that elicits cellular transformation by acting on multiple targets, including members of the retinoblastoma tumor suppressor family (pRb, p107, and p130), members of the CBP-family of transcriptional coactivators (CBP, p300, and p400), and the tumor suppressor, p53. T antigen sequences important for transformation have been mapped to two different regions of the molecule: the amino-terminal domain, which encompasses the first 125 amino acids, and a region located within the carboxy-terminal half of the molecule (FIG. 1).

Evidence that one or more independent transforming functions reside in the carboxy-terminal half of T antigen stems from the observation that carboxy-terminal fragments of T antigen have the ability to immortalize primary C57B1/6 mouse embryo fibroblasts (Cavender et al. (1995) *J. Virol.* 69:923). This activity maps to a bipartite region including amino acids 351–450 and 533–626 that correspond to sequences required for T antigen association with p53 (Kierstead et al. (1993) *J. Virol.* 67:1817). This same region has been shown to be necessary for T antigen association with CBP, p300, and p400 (Eckner et al. (1996) *Mol. Cell. Biol.* 12:3288). It is not clear whether the CBP-family proteins bind directly to T antigen, or indirectly by associating with T antigen-bound p53.

The amino-terminal region of T antigen also carries independently acting transforming functions since it is capable of immortalizing primary cells, transforming established cell lines in culture, and inducing tumors in transgenic mice (Chen et al. (1992) *Oncogene* 7:1167; Clayton et al. (1982) *Nature* 299:59; Colby et al. (1982) *Proc. Nat'l. Acad. Sci. USA* 79:515189; Srinivasan et al. (1989) *J. Virol.* 63:5459). Three separate sequence motifs within the amino-terminal domain contribute to transformation. First, the sequence extending from amino acids 101–118 is similar to the cr2 motif found in adenovirus E1A proteins, and papillomavirus E7 proteins (Chen et al. (1990) *J. Virol.* 64:3350). This sequence is required for the association of T antigen with the three members of the retinoblastoma tumor suppressor family of proteins: pRb, p107, and p130 (DeCaprio et al. (1988) *Cell* 54:275). Second, a region near the amino-terminus of T antigen (amino acids 17–32) is similar to the cr1 motif found in adenovirus E1A proteins. Deletion of this sequence alters the transforming properties of T antigen, but a cellular target for this region has not been identified (Pipas et al. (1983) *Mol. Cell. Biol.* 3:203; Symonds et al. (1993) *Mol. Cell. Biol.* 13:3255). Finally, mutations within or near a hexapeptide (HPDKGG; amino acids 42–47 of SEQ ID NO: 1) conserved among the T antigens in all known polyomaviruses render T antigen transformation-defective (Peden et al. (1992) *Virus Genes* 6:107).

The amino-terminal 82 amino acids of T antigen are similar to the J domain of the DnaJ family of molecular chaperones (Kelley et al. (1994) *TIBS* 19:277). This similarity includes the HPDKGG motif (amino acids 42–47 of SEQ ID NO: 1) as well as the cr1-like sequence (FIG. 1). Since the 82 amino-terminal amino acids of large T antigen and small t antigen are identical, the J-domain homology region is included in small t as well. One function of J-domain containing chaperones is to interact with, and modulate the activity of, a specific member of the DnaK family (reviewed by Caplan et al. (1993) *Mol. Biol. Cell* 4:555; Hartl, (1996) *Nature* 381:571). The cytosolic mammalian DnaK homologue, hsc70, associates with T antigen through its amino-terminal domain (Sawai et al. (1989) *J. Virol.* 63:3691; Campbell et al. (1997) *Genes & Devel.* 11:1098–1110; Sawai et al. (1994) *Virus Res.* 31:367–378).

Mutations within the J-domain region of T antigen affect diverse viral functions including DNA replication, transcriptional regulation, virion assembly, and tumorigenesis (Pipas et al. (1983); Peden, (1992); Srinivasan et al. (1989) *J. Virol.* 63:5459; Spence et al. (1994) *Virology* 204:200). Other reports suggest a role for the T antigen/hsc70 association in stimulating the degradation of the tumor suppressors p107 and p130 (Stubdal et al. (1996) *J. Virol.* 70:2781; Harris et al. (1996) *J. Virol.* 70:2378; Stubdal et al. (1997) *Mol. Cell. Biol.* 17:4979–4990).

A collection of T antigen mutants with altered amino acids within each of the known sequence motifs important for transformation have been studied in an attempt to characterize the roles of T antigen in transformation. Mutant d11135 contains a deletion of amino acids 17 through 27 and synthesizes a T antigen lacking the cr1-like motif, and fails to transform established cell lines and to immortalize primary cells (Pipas et al. (1983); Michalovitz et al. (1987) *J. Virol.* 61:2648). On the other hand, d11135 induces T cell lymphomas in transgenic mice at the same efficiency as wild-type T antigen (Symonds et al. (1993) *Mol. Cell. Biol.* 13:3255). Even though d11135 is defective for viral DNA replication in vivo, the purified mutant protein supports the replication of viral DNA in vitro nearly as well as wild-type (Collins et al. (1995) *J. Biol. Chem.* 270:15377). Mutant 5110 carries a single amino acid substitution of D44N within the conserved HPDKGG motif (amino acids 42–47 of SEQ ID NO: 1), and has a reduced ability to transform established cell lines. Mutant 3213 containing two amino acid substitutions (E107K, E108K) within the cr2-like sequences, is defective for T antigen association with pRb.

The foregoing studies with these mutants suggest that T antigen's contribution to cellular transformation is complex. An elucidation of the role of the J-domain homology region of T antigen in transformation and chaperone action is necessary to devise strategies to interfere with viral and nonviral tumorigenicity.

SUMMARY OF THE INVENTION

The present invention provides a method of identifying agents that interfere with the interaction of a J-domain and a DnaK protein. In one embodiment, agents are identified by measuring their ability to block the stimulation of the ATPase activity of a DnaK protein by a polypeptide comprising a J-domain. In another embodiment, agents are identified by measuring their ability to block the J-domain-catalyzed release of a denatured polypeptide substrate from a DnaK protein. In a preferred embodiment, the polypeptide comprising a J-domain comprises amino acids 1–82 or amino acids 1–136 of the SV40 large T antigen, and the DnaK protein is the yeast Ssa1p protein or the human hsc70 protein. In another embodiment, agents are identified by measuring their ability to block the J-domain dependent growth of the *S. cervisiae* mutant ydj1-151 at elevated temperatures.

The present invention further provides a compartmentalized kit comprising a first container containing a polypeptide comprising a J-domain and a second container containing a DnaK protein. In another embodiment, the kit further comprises a third container containing a denatured polypeptide substrate for a DnaK protein.

BRIEF DESCRIPTION OF THE DRAWINGS

FIGS. 1A–1D depict the structure of the SV40 large T and small t antigens.

FIG. 1A and FIG. 1B depict the domain structure of the 708 amino acid large t antigen and the 174 amino acid small t antigen, respectively.

FIG. 1C depicts the structure of the TN136 protein (pTN136).

FIG. 1D provides an alignment of T antigen with the J-domain of several DnaJ homologs.

DETAILED DESCRIPTION OF THE INVENTION

Figures 1C, 1D:
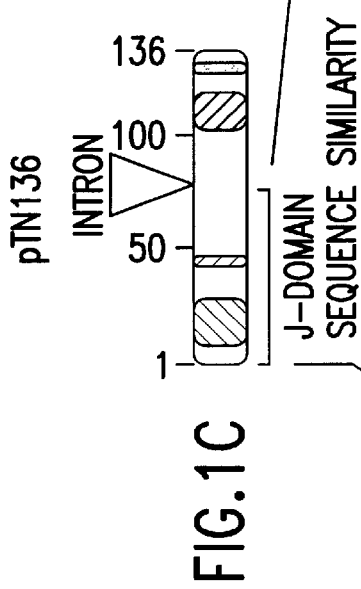

Simian virus 40 (SV40) is a small DNA virus that induces tumors in a variety of test animals. The tumorigenic potential of SV40 is provided by two viral proteins, the large T antigen (T antigen) and the small t antigen (t antigen). The T antigen is a 708 amino acid multifunctional protein having a domain structure as depicted in FIG. 1. The N-terminal region of T antigen shares sequence homology with the universally conserved DnaJ family of chaperone proteins. In particular, T antigen comprises an N-terminal J-domain that is also present in the members of the DnaJ family. The DnaJ family of proteins includes dnaJ from *E. coli*, Ydj1p from *S. cerevisiae*, and hsc40 from humans.

It has been discovered in accordance with the present invention that truncated forms of T antigen that contain the J-domain and are sufficient for transformation are capable of stimulating the ATPase activity of members of the DnaK class of chaperone proteins (DnaK proteins). Members of this class include DnaK from *E. coli*, Ssa1p from *S. cerevisiae*, and hsc70 from humans. The present invention thus implicates the activation of DnaK proteins by the T antigen J-domain in transformation by SV40. Agents that interfere with the activation of DnaK proteins by the T antigen J-domain are thus useful as antiviral agents.

For example, agents that block the ability of the T antigen J-domain to interact with a DnaK protein are useful for the treatment of progressive multifocal leukoencephalopathy (PML). PML, a fatal degenerative disease of the central nervous system, is caused by infection of the brain by SV40 or a related polyomavirus, JC virus (JCV). SV40 and JCV replicate in immunocompromised humans, such as patients with Hodgkin's lymphoma, chronic lymphocytic leukemia, AIDS, and in allograft recipients.

It has been further discovered in accordance with the present invention that the truncated forms of T antigen are capable of dissociating a permanently unfolded polypeptide from a DnaK chaperone protein. Thus T antigen possesses two hallmarks of a DnaJ chaperone, i.e. the ability to stimulate the ATPase activity of a DnaK chaperone, and the ability to catalyze release of a polypeptide substrate from a DnaK chaperone. In SV40-mediated tumorigenicity, T antigen thus mimics the chaperone action of a DnaJ protein by its action on a DnaK protein. Further, the interaction of T antigen with a DnaK protein is required for the subsequent inactivation of cellular tumor suppressors. The disruption of this interaction blocks the inactivation of tumor suppressor proteins that in turn leads to tumorigenesis. The present discoveries thus indicate that the activation of a DnaK protein by a J-domain is implicated in tumorigenicity. Accordingly, the present method of identifying agents that disrupt the J-domain/DnaK protein interaction permits the identification of compounds that are useful as anti-tumor agents.

One embodiment of the present invention provides a method of identifying agents that interfere with the interaction of a DnaK protein and a polypeptide comprising a J-domain. Agents are identified by their ability to block the stimulation of the ATPase activity of a DnaK protein by a polypeptide comprising a J-domain. The present method comprises contacting a polypeptide comprising a J-domain with a DnaK protein in the presence of ATP and in the absence of an agent to be tested for its ability to block the stimulation of ATPase activity; determining the stimulation of ATPase activity of the DnaK protein by the polypeptide comprising the J-domain; contacting the polypeptide comprising a J-domain with the DnaK protein in the presence of ATP and in the presence of an agent to be tested for its ability to block the stimulation of ATPase activity; determining the stimulation of ATPase activity of the DnaK protein by the polypeptide comprising the J-domain in the presence of the agent to be tested; and comparing the stimulation of ATPase activity in the absence and presence of the agent to be tested, wherein a decrease in ATPase activity in the presence of the agent indicates an agent that interferes with the activation of a DnaK protein by a protein comprising a J-domain.

In accordance with the present invention, a J-domain is a term understood in the art to define a region of homology in the DnaJ family of proteins and the N-terminal region of SV40 T antigen. Representative J-domains are disclosed by Cyr et al. (1994) *Trends in Biochemical Sciences* 19:176, Silver et al. (1993) *Cell* 74:5, Kelley et al. (1994) *Trends in Biochemical Sciences* 19:277, and Caplan et al. (1993) *Mol. Biol. Cell* 4:555, the disclosures of which are incorporated herein by reference. J-domains generally comprise from about seventy to about eighty amino acids. J-domains included within the scope of the present invention are the J-domains from T-antigen, human Hsp40, Hdj1, Hdj2, and Hsj1, *S. cerevisiae* Ydj1p, Scj1, Sec 63, Sis1 and Zuotin, *E. coli* DnaJ, cucumber J-domain, archaebacteria J-domain, and others for example as disclosed by Silver et al. and Caplan et al. Polypeptides having at least about 50% amino acid identity, and preferably at least about 80% amino acid identity, to the enumerated sequences and maintaining the ability to stimulate the ATPase activity of hsc70 are also included within the definition of J-domains in accordance with the present invention. Amino acid identity is determined by the University of Wisconsin Genetics Computer Group program Best-Fit, as described for example by Devereux et al. (1984) *Nucleic Acids Res.* 12:387. In a preferred embodiment, the J-domain is the SV40 T antigen J-domain having the following amino acid sequence (SEQ ID NO:1):

MDKVLNREESLQLMDLLGLERSAWGNIPLMRK AYLKKCK-
EFHPDKGGDEEKMKKMNTLYKKMEDGVKYAH QPDFG-
GFWDATE

A polypeptide comprising a J-domain is defined in accordance with the present invention as the J-domain alone, or with part or all of the remainder of its native amino acid sequence, or with other amino acid sequences. In a preferred embodiment, the polypeptide containing a J-domain does not have intrinsic ATPase activity. In another preferred embodiment, a polypeptide comprising a J-domain comprises amino acids 1–82 of T antigen (SEQ ID NO: 1). In another preferred embodiment, a polypeptide comprising a J-domain is composed of amino acids 1–136 of T antigen as set forth below (SEQ ID NO: 2):

MDKVLNREESLQLMDLLGLERSAWGNIPLMRK AYLKKCK-
EFHPDKGGDEEKMKKMNTLYKKMEDGVKYAH QPDFG-
GFWDATEIPTYGTDEWEQWWNAFNEENLFCSEEM PSSD-
DEATADSQHSTPPKKKRKVEDPK

Polypeptides containing a J-domain can be made by methods known to those of ordinary skill in the art. For example, a protein containing a J-domain may be purified from its native source, and the protein subjected to chemical or enzymatic cleavage to provide a polypeptide containing a J-domain. Alternately, a polypeptide containing a J-domain may be chemically or recombinantly synthesized by methods known in the art. For example, recombinant baculoviruses expressing nucleic acids encoding the J-domain of T antigen may be used to infect insect cells, and the polypeptide products thereof may be purified from the baculovirus-infected cells by immunoaffinity chromatography using T antigen specific monoclonal antibodies.

In accordance with the present invention, a DnaK protein is defined as a member of a conserved family of proteins that includes the constitutively expressed mammalian heat shock protein hsc70, *E. coli* DnaK, and *S. cerevisiae* Ssa1p. DnaK proteins are characterized by intrinsic ATPase activity and polypeptide binding domains. Mammalian hsc70 may be purified by methods known in the art and described for example by Cheetham et al. (1994) *Eur. J. Biochem.* 226: 99, incorporated herein by reference, or may be obtained commercially, for example from StressGen, Inc. Victoria, British Columbia, Canada. Ssa1p may be purified by methods known to those of ordinary skill in the art and disclosed for example by Brodsky et al. (1993) *J. Cell Biol.* 120:95, the disclosure of which is incorporated herein by reference. DnaK may be purified by methods known to those of ordinary skill in the art and disclosed for example by Jordan et al. (1995) *J. Biol. Chem.* 270:4563, the disclosure of which is incorporated herein by reference. DnaK proteins from other species are also included herein.

In accordance with the present method, a polypeptide comprising a J-domain is contacted with a DnaK protein in the presence of ATP, and the stimulation of ATPase activity of the DnaK protein by the polypeptide comprising the J-domain is determined. Stimulation of ATPase activity is determined by calculating the difference in ATPase activity of the DnaK protein before and after contact with the polypeptide comprising the J-domain. If the polypeptide having the J-domain has inherent ATPase activity, that inherent activity is subtracted when determining stimulation of ATPase activity. ATPase activity can be measured by methods known to those of skill in the art, for example by measuring the production of ADP and/or free phosphate that result from the hydrolysis of ATP. In a preferred embodiment, ATPase activity is measured by including in the assay ATP that has been labeled on its a phosphate, and then monitoring the appearance of a phosphate-labeled ADP. ADP is easily detectable by chromatography because it migrates apart from ATP.

In a preferred embodiment of the present invention, ATPase activity is measured by including $\alpha$-[$^{32}$P]-ATP in the assay, and measuring the production of $\alpha$-[$^{32}$P]-ADP. ADP formation may be assayed by one-dimensional chromatography on cellulose or silica gel thin layer chromatograms, including polyethyleneimine (PEI)-cellulose or PEI-silica plates. The amount of liberated $\alpha$-[$^{32}$P]-ADP is then quantified, for example by phosphoimage analysis of the resulting chromatogram. A representative assay is disclosed by Cyr et al. (1992). *J. Biol. Chem.* 267:20927, the disclosure of which is incorporated herein by reference.

After the stimulation of ATPase activity of the DnaK protein by the polypeptide comprising the J-domain is determined, the steps of the assay are repeated in the presence of an agent to be tested for its ability to block the stimulation of the ATPase activity. A decrease in stimulated ATPase activity in the presence of the agent is indicative of an agent that interferes with the activation of a DnaK protein by a protein comprising a J-domain. A reduction in stimulated ATPase activity of at least about 20% in the presence of the agent is considered to be a decrease in ATPase activity in accordance with the present invention.

The assay is conducted in an aqueous buffer compatible with an ATPase assay and known to those of ordinary skill in the art. Suitable buffers include a buffer containing 50 mM HEPES, pH 7.4, 50 mM NaCl, 10 mM DTT and 2 mM MgCl$_2$. The relative amounts of the components of the assay, including the polypeptide comprising the J-domain, the DnaK protein, the agent to be tested, and ATP can be determined by those of ordinary skill in the art. In a preferred embodiment, an equimolar amount or molar excess of the polypeptide containing the J-domain is used relative to the DnaK protein. In a preferred embodiment, the assay contains 1 $\mu$g Ssa1p, and 1 $\mu$g TN136 in a 20 $\mu$l reaction volume, which is incubated for 30–60 minutes at 30° C.

In a preferred embodiment of the method of the present invention, the polypeptide comprising a J-domain comprises the amino terminal domain of T antigen and, more particularly, amino acids 1–82 of T antigen. In accordance with the present invention, a vector designated TN136 has been constructed that expresses the amino-terminal 136 amino acids of T antigen. TN136 contains T antigen cDNA, into which a stop codon has been placed immediately following codon 136, under the control of the RSV promoter. Recombinant baculoviruses expressing the TN136 protein were generated by standard protocols such as those described by Lanford (1988) *Virology* 167:72, and used to infect insect cells. TN136 protein was purified from the baculovirus-infected insected cells by immunoaffinity chromatography using T antigen specific monoclonal antibodies. The TN136 protein includes a J-domain, lacks ATPase activity and stimulates the ATPase activity of DnaK proteins including mammalian hsc70, *E. coli* dnaK, and *S. cerevisiae* Ssa1p. The TN136 protein typically stimulates the ATPase activity of Ssa1p by about 8-fold, and the ATPase activity of hsc70 by about five-fold.

In a representative assay conducted in accordance with the method of the present invention, purified TN136 protein is mixed with a purified DnaK protein and $\alpha$-[$^{32}$P]-ATP in a buffer containing $Mg^{2+}$-ATP. In a preferred embodiment the DnaK protein is Ssa1p. The reaction mixture is incubated at 30° C. for 30–60 minutes. ATPase activity is then determined by measuring the hydrolysis of ATP as monitored by the appearance of $\alpha$-[$^{32}$P]-ADP. The $\alpha$-[$^{32}$P]-ADP is measured by applying an aliquot of the reaction mixture to a silica gel or cellulose PEI thin layer chromatography plate. The thin layer chromatography plate may be prespotted with a mixture of ATP and ADP in order to conveniently determine the expected migration position of $\alpha$-[$^{32}$P]-ADP. The amount of liberated $\alpha$-[$^{32}$P]-ADP is then quantified, for example by obtaining a phosphoimage analysis of the chromatogram or by cutting out the spots containing $\alpha$-[$^{32}$P]-ADP and determining radioactivity by liquid scintillation counting. The assay is then repeated in the presence of an agent to be tested for its ability interfere with the activation of a DnaK protein by a polypeptide comprising a J-domain. The amount of $\alpha$-[$^{32}$P]-ADP released in the absence and presence of the agent is compared in order to identify agents that block the stimulation of the ATPase activity of the DnaK protein by the TN136 protein.

Those of ordinary skill in the art can determine suitable concentrations of reactants and suitable assay conditions for the measurement of ATPase activity. For example, in a representative assay, 1 $\mu$g purified TN136 protein is mixed with 1 $\mu$g Ssa1p and $\alpha$-[$^{32}$P]-ATP in a buffer containing 50 $\mu$M $Mg^{2+}$-ATP. Under these conditions, an 8-fold stimulation of the Ssa1p ATPase by TN136 is typically observed.

It has been determined in accordance with the present invention that a polypeptide comprising a J-domain of T antigen, in the presence of ATP, catalyzes the release of a denatured polypeptide substrate from a DnaK protein. Accordingly, in another embodiment of the present invention, agents that interfere with the interaction of the J-domain with a DnaK protein are identified by measuring the ability of the agents to block the J-domain-catalyzed release of a polypeptide substrate from a DnaK protein.

The method comprises comparing the amount of J-domain-catalyzed release of a denatured polypeptide substrate from a DnaK protein in the presence and absence of an agent to be tested, whereby a decrease in the amount of substrate released in the presence of the agent is indicative of the identification of an agent that interferes with the interaction between a J-domain and a DnaK protein. A decrease in the amount of substrate released of at least about 20% in the presence of the agent is considered to be a decrease that indicates the identification of an agent that interferes with the interaction of a J-domain with a DnaK protein.

The method of identifying agents that interfere with the interaction of a J-domain and a DnaK protein may be conducted by contacting a DnaK protein with an unfolded polypeptide substrate under conditions whereby the substrate binds to the DnaK protein, and determining the amount of substrate bound to the DnaK protein; adding a polypeptide comprising a J-domain and ATP and measuring the amount of substrate released from the DnaK protein in the absence of the agent to be tested; contacting a DnaK protein with an unfolded polypeptide substrate, a polypeptide comprising a J-domain and ATP in the presence of an agent to be tested for its ability to block the J-domain-catalyzed release of polypeptide substrate from a DnaK protein, and measuring the amount of substrate released in the presence of the agent to be tested; and comparing the amount of substrate released in the presence and absence of the agent to be tested, whereby a decrease in the amount of substrate released in the presence of the agent is indicative of the identification of an agent that interferes with the interaction between a J-domain and a DnaK protein.

DnaK proteins and polypeptides comprising a J-domain are defined as disclosed hereinabove for assays that measure ATPase activity. A denatured polypeptide substrate is any denatured polypeptide capable of binding to a selected DnaK protein and capable of being at least partially released from the DnaK protein in the presence of a polypeptide comprising a J-domain and ATP. Suitable denatured polypeptide substrates include, for example, carboxymethyl lactalbumin (CMLA), thermally unfolded firefly luciferase, chemically denatured rhodanese, and peptide C of vesicular stomatitis virus glycoprotein.

Binding and release of the denatured polypeptide substrate can be determined by methods known in the art, for example, by gel shift assays using a labeled polypeptide substrate. For example, the binding of $^{125}$I-CMLA to a DnaK protein and its release in the presence of ATP and a polypeptide comprising a J-domain can be measured by a gel shift assay as described for example by Cyr et al. (1992) *J. Biol. Chem.* 267:20927; Cheetham et al. (1994) *Eur. J. Biochem.* 226:99 and Srinivasan et al. (1997) *Molec. Cell. Biol.* 17:4761–4773, the disclosures of which are incorporated herein by reference. The binding of the DnaK protein to the labeled substrate is monitored by the retarded mobility of the labeled substrate by SDS-polyacrylamide gel electrophoresis (SDS-PAGE). $^{125}$I-CMLA alone migrates with high mobility on native polyacrylamide gels, while $^{125}$I-CMLA bound to DnaK protein migrates at a position approximately coincident to that of the DnaK protein. The amount of CMLA bound to the DnaK protein or released therefrom can be quantitated by known methods, for example by excising bands on the gel corresponding to $^{125}$I-CMLA-DnaK and $^{125}$I-CMLA, and assaying for $^{125}$I by gamma counting.

In another embodiment of the present invention, agents that interfere with the interaction of a J domain and a Dnak protein are identified by their ability to block the growth of a genetically engineered yeast strain. The *S. cerevisiae* mutant ydj1-151 (Caplan et al. (1992) *Cell* 71:1143–1155), obtained from Dr. Avron J. Caplan, is a temperature-sensitive mutant that fails to grow at elevated temperatures, for example at or above 35° C., due to a mutation that renders Ydj1p, a yeast DnaJ protein, defective. It has been found in accordance with the present invention that ydj1-151 cells that have been engineered to express a polypeptide comprising the J-domain of SV40 T antigen fused to the non J-domain of Ydj1p are capable of growth at 37° C., and thus that the J-domain of T antigen has rescued the ydj1-151 defect. The present invention provides *S. cerevisiae* ydj1-151 cells comprising a polypeptide comprising the J-domain of SV40 T antigen. In a preferred embodiment, the J-domain has the amino acid sequence of SEQ ID NO: 1 or SEQ ID NO: 2. In another preferred embodiment, the polypeptide comprising the J-domain is a hybrid polypeptide in which the J-domain of Ydj1p has been replaced by the J-domain of SV40 T antigen. In a particularly preferred embodiment, the polypeptide is a hybrid polypeptide in which amino acids 1 through 70 of Ydj1p (as numbered from the amino terminus of Ydj1p) have been replaced by amino acids 1 through 82 of T antigen, which hybrid polypeptide has been designated herein as T-Ydj1p.

In another preferred embodiment, ydj1-151 cells that express a polypeptide comprising the J-domain of SV40 T antigen have been engineered for regulated expression of the polypeptide. Galactose-inducible promoter systems are particularly preferred.

The ydj1-151 cells comprising a polypeptide comprising the J-domain of SV40 T antigen can be made by methods known to those of ordinary skill in the art. For example, a yeast expression vector containing DNA encoding the polypeptide is constructed and introduced into ydj1-151 cells by standard methods of yeast transformation. In a preferred embodiment, vectors are constructed to achieve regulated expression of the polypeptide. Galactose-inducible promoter systems are particularly preferred. Galactose regulation of foreign gene expression is well known to those or ordinary skill in the art, and described for example in Schneider et al. (1991) *Methods Enz.* 194:373–388, Romanos et al. (1992) *Yeast* 8:423 and Ausubel et al. (1995) *Current Protocols in Molecular Biology,* John Wiley and Sons, the disclosures of which are incorporated herein by reference.

Galactose regulation of expression of T-ydj1p in ydj1-151 cells may be achieved, for example, by inserting the fusion protein containing amino acids 1–82 of T antigen into Ydj1p such that the first 70 amino acids of Ydj1p were replaced with the T antigen (1-82) fragment. The cloning was achieved by two rounds of PCR. The first round inserted an EcoR1 site in the DNA encoding the N terminus of the T antigen DnaJ domain and a Not1 site in the DNA encoding C terminus of Ydj1, as well as complementing regions at the junction of the DnaJ domains and the rest of the proteins. The products were annealed and a second round of PCR using the N and C end DNA primers was used to obtain full length genes encoding the fusion proteins. The genes were placed into the pYes2 expression vector from Stratagene at the EcoR1 and Not1 sites and transformed into the ydy1-151 strain using lithium acetate-mediated transformation (Rose et al., 1990). Cells were grown on selective medium (Sc-ura) containing 2% glucose to select for transformants, and to express the fusion protein, were re-plated onto Sc-ura medium containing 2% galactose. Cells were grown at the permissive temperature for ydj1 mutant cells (26° C.) unless the ability of the fusion protein to rescue the ydj1 mutations was assayed, in which case the plates were incubated at 26° C., 30° C., 35° C., and 37° C.

The ydj1-151 cells that express a polypeptide comprising the J-domain of T antigen, referred to herein as T-dependent ydj1-151 cells, are useful in a method of identifying an agent that interferes with the interaction of a J-domain and a DnaK protein. Agents are identified by their ability to inhibit the growth of T-dependent ydj1-151 cells at 37° C., but not at 25° C. A reduction in cell growth or rate of growth of at least about 20%, as measured by spectrophotometric analysis at 600 nm (which measures the turbidity in growth medium), is considered to be an inhibition of growth in accordance with the present method. The present method comprises growing T-dependent ydj1-151 cells at a temperature of from about 20 to about 30° C., and preferably about 25° C., under conditions suitable for cell growth, in the absence and presence of an agent to be tested for its ability to interfere with the interaction of a J-domain and a DnaK protein; elevating the temperature to at or above 35° C., and preferably to about 37° C.; measuring the growth of T-dependent ydj1-151 cells; and comparing growth of T-dependent ydj1-151 cells in the absence and presence of the agent, wherein a reduction in growth in the presence of the agent at or above 35° C. is indicative of an agent that blocks the interaction of a J-domain and a DnaK protein. Conditions for yeast cell growth are well-known to those of ordinary skill in the art and described in various laboratory manuals, including for example Rose et al. (1990) *Methods in Yeast Genetics: Laboratory Course Manual.* Cold Spring Harbor Laboratory Press, Cold Spring Harbor, N.Y. and Ausubel, (1995) *Current Protocols in Molecular Biology,* John Wiley and Sons, the disclosures of which are incorporated by reference. Yeast cell growth can be measured by standard methods, including for example spectrophotometric analysis of turbidity in growth medium at 600 nm.

A preferred embodiment of the present method utilizes ydj1-151 cells containing DNA encoding T-Ydj1p under the control of a galactose-inducible promoter system, which cells are referred to herein as T-Ydj1p-dependent ydj1-151. The T-Ydj1p-dependent ydj1-151 cells, when grown in the presence of a non-galactose sugar source, for example glucose, are capable of growth at 25° C. but not at 37° C. In the presence of galactose, the T-Ydj1p-dependent ydj1-151 cells are capable of growth at 25° C. and 35° C. and grow poorly at 37° C. It has been discovered herein that the SV40 T antigen J-domain has rescued the ydj1-151 defect, thus allowing some growth at 37° C. and wild-type growth at 35° C.

Accordingly, the T-Ydj1p-dependent ydj1-151 cells provide a yeast system for identifying agents that interfere with the interaction of the J-domain of the SV40 large T antigen with a DnaK homologue. Agents are identified by their ability to block the growth of T-Ydj1 p-dependent ydj1-151 cells in the presence of galactose at temperatures at or above 35° C., while not affecting growth at 25° C. The present method comprises growing T-Ydj1p-dependent ydj1-151 at a temperature of from about 20 to about 30° C. in the presence of galactose and in the presence and absence of an agent to be tested for its ability to interfere with the interaction of a J-domain and a DnaK protein; elevating the temperature to at or above 35° C., and preferably to about 37° C.; and measuring growth of T-Ydj1p-dependent ydj1-151 cells in the absence and presence of the agent wherein a reduction in growth at temperatures at or above 35 ° C. in the presence of the agent is indicative of the identification of an agent that interferes with the interaction of the J-domain of SV40 large T antigen and a DnaK homologue. Yeast cell growth can be assessed by methods known to those of ordinary skill in the art, including for example spectrophotometric analysis of turbidity in growth medium at 600 nm.

The creation of hybrid T antigen molecules, such as T-Ydj1p, that are functional in yeast provides the basis for a novel genetic screen to (1) identify cellular partner proteins from any animal source of the T antigen DnaJ domain that are necessary for its activity and specificity and (2) generate novel mutations in the T antigen DnaJ domain. The basis for this screen is the expression of the fusion protein using the galactose-inducible system in the ydj1-151 mutant strain, described above.

Expressing a mutant version of the T-Ydj1p fusion protein results in the temperature growth defect not being rescued by growing the cells on galactose. The use of such mutants forms the basis for a screen for mammalian or yeast proteins that when over-expressed restore the ability of the mutant protein (T-Ydj1p) to function, as assayed by cell growth on galactose at 35° C. Such screening techniques are known to those in the art as a multi-copy suppressor screen that is commonly used in yeast genetics to identify interacting proteins or other factors (See, e.g. Rose et al. (1990) *Methods in Yeast Genetics: A Laboratory Manual.* Cold Spring Harbor Press, Cold Spring Harbor, N.Y., incorporated herein by reference). These factors may be novel targets for drug-based anti-viral and anti-tumorigenetic therapies.

Random mutation of the chaperone domain (e.g. by error-prone PCR mutagenesis) of the wild type fusion protein (T-Ydj1p) gene, which is then expressed in the ydj1-151 mutant strain, can indicate mutations that affect the chaperone function. These mutations are identified as those that no longer rescue the ydj1-151 mutant grown on galactose at 35° C. Such new mutations in the T antigen DnaJ domain may indicate important sites in the molecule that are vital for transformation and/or viral replication.

The present invention further provides a compartmentalized kit comprising a first container containing a polypeptide containing a J-domain and a second container containing a DnaK protein. In a preferred embodiment the polypeptide containing a J-domain is a polypeptide containing the J-domain from T-antigen, human Hsp40, *S. cerevisiae* Ydj1p, or *E. coli* DnaJ, or a J-domain having at least about 50% amino acid identity, and preferably at least about 80% amino acid identity, to the enumerated sequences and maintaining the ability to stimulate the ATPase activity of hcs70. In another preferred embodiment, a polypeptide comprising a J-domain comprises amino acids 1–82 of T antigen (SEQ ID NO: 1). In another preferred embodiment, a polypeptide comprising a J-domain is composed of amino acids 1–136 of T antigen (SEQ ID NO:2). In another preferred embodiment, the DnaK protein is mammalian hsc70, *E. coli* DnaK, or *S. cerevisiae* Ssa1p.

The present invention further provides a compartmentalized kit comprising a first container containing a polypeptide containing a J-domain, a second container containing a DnaK protein, and a third container containing a denatured polypeptide substrate. In a preferred embodiment, the substrate is CMLA. The present kits are useful to conduct a method of identifying agents that interfere with the activation of a DnaK protein by a polypeptide comprising a J-domain.

The following examples further illustrate the present invention.

EXAMPLE 1

Expression and Purification of Mutant and Truncated T Antigen

Plasmids containing a cDNA or genomic version of wild-type or mutant T antigen under the control of the RSV LTR promoter or the SV40 early promoter were derived from pSV-B3 or a related vector as described by Peden et al. (1980) *Science* 209:1392. The plasmids also contain a G418 resistance gene under the control of the SV40 early promoter. Plasmid TN136 comprises a truncated version of SV40 T antigen gene and directs the synthesis of the first 136 amino acids of T antigen, including the amino-terminal transforming domain. TN136 was generated by placing a stop codon immediately following codon 136 of a T antigen cDNA. Briefly, the first 136 codons of the large T antigen gene were amplified from pVL941-T, a plasmid containing a full-length cDNA insert of the full-length T antigen gene. The 5'PCR primer contained a BamHI site. The 3'primer contained a stop codon following codon 136 and an XbaI site. The amplified fragment was then inserted into the appropriate expression vector.

Various mutations designed to alter one of the three conserved sequence motifs (cr1, HPDKGG and cr2) depicted in FIG. 1 were engineered into the full-length and truncated T antigens. Mutations of the p53 binding domain and the ATP binding domain were engineered into full length T antigen. SV40 mutants dl1135 (Δ17–27), 3213 (E107K, E108K), K1 (E107K), 5110 (D44N) and 5061 (G431—A, L, E) have been described by Pipas et al. (1983) *Mol. Cell. Biol.* 3:203; Peden et al. (1992) *Virus Genes* 6;107; and Farber et al. (1987) *J. Virol.* 61:436. 5030 (P417S) is an ATPase-defective mutant constructed by standard methods. The TN136/5110, TN136/3213 and TN136/K1 double mutants were generated by replacing the Asp718-Bbs1 fragment in TN136 with the corresponding sequences from the appropriate mutant plasmid.

Recombinant baculoviruses directing the synthesis of mutant T antigens were generated following standard protocols are described by Lanford et al. (1988) *Virology* 167:72 and used to infect *Spodoptera frugiperda* Sf9 or High Five™ cells. The T antigen variants were purified from the baculovirus-infected insect cells by immunoaffinity chromatography as described by Dixon et al. (1985) *J. Virol.* 53:1001, Lanford (1988), and Simanis (1985) *Virology* 144:88. T antigen specific monoclonal antibodies PAb416 or PAb419 (Harlow et al. (1981) *J. Virol.* 39:861) were routinely used for this purpose; dl1135 was purified using the KT3 antibody described by Collins et al. (1995) *J. Biol. Chem.* 270: 15377. Antibodies were purified from hybrodima supernatants or from mouse ascites fluid and then coupled to Protein A-Sepharose or Protein G-Sepharose (Pharmacia). Purified T antigen was dialyzed against 10 mM Tris pH 8.0, 100 mM NaCl, 1 mM EDTA, 1 mM DTT and 50% glycerol and stored at −20° C. Following SDS-polyacrylamide gel electrophoresis, the purity and integrity of each T antigen preparation was assessed by silver staining and Western blot analysis and determined to be greater than 90%.

EXAMPLE 2

Ability of T Antigen Mutants to Induce Morphological Transformation

The ability of the mutants of Example 1 to induce morphological transformation of two established cell lines, C3H10T1/2 and REF52, was examined. C3H10T1/2 and REF52 are fibroblastic cell lines established from mouse and rat embryos, respectively.

REF52 or C3H10T1/2 cells were transfected with vectors produced in Example 1 that express wild-type or mutant T antigen gene using either the RSV LTR or SV40 early promoter, and that co-express a marker for G418 resistance. (Identical results were achieved when the CMV intermediate early promoter was used to drive T antigen gene expression.)

REF52 or C3H10T1/2 cells were plated at a density of $5 \times 10^5$ cells per 10 cm dish approximately 24 hours prior to transfection. The cells were fed with fresh medium containing 20% FBS 4–6 hours prior to transfection. $CaPO_4$/DNA precipitates were applied directly to the medium as described by Graham et al. (1973) *Virology* 52:456. After incubation at 37° C. for 4 hours, the cells were washed twice with 5 ml medium and treated with 5 ml 15–20% glycerol for 1 minute. The cell monolayer was then rinsed with 5 ml Hepes buffered saline, and incubated in MEM supplemented with 10% FSB at 37° C. Following transfection the cells were split to duplicate dishes.

In order to assay for dense focus formation, transfected REF52 or C3H10T1/2 cells were maintained for about four weeks with media changes every third or fourth day. Plates were scored visually for foci following staining with Geimsa in acetone, or assessed visually under a microscope. Foci appeared at about three weeks post transfection in dishes transfected with plasmids expressing DNA coding for wild-type T antigen. When the dominant selection marker, G418 (Genatamycin sulfate), was used, the transfected cells were split into medium containing the antibiotic 48 hours post-transfection and maintained in medium plus antibiotic for 16–18 days, with twice weekly changes of medium. Antibiotic resistant colonies were clearly visible in two weeks. The transformation phenotypes were scored at about three weeks post-transfection and expressed as a ratio of trans-formed versus flat colonies. Transfected cells were also examined for T antigen expression, p53, pRb and p107 by immunoprecipitation and immunoblotting. Exponentially growing cells were washed with phosphate buffered saline (PBS) and either lysed immediately or frozen at −70° C. for later use. Pellets were lysed in lysis buffer containing 50 mM Tris-HCl, pH 8, 5mM EDTA, 150 mM NaCl, 0.5% NP40 for 20 minutes on ice. Clarified extracts containing equal amounts of protein were immunoprecipitated with the appropriate antibodies for 1 hour at 4° C. Immunoprecipitates were collected using Protein-A sepharose and washed three times in SNNTE (5% Sucrose, 1% NP40, 0.5M NaCl, 50 mM TrisHCl pH 7.5 and 5 mM EDTA) and once with NTE (50 Mm NaCl, 1 mM TrisHCl pH 7.5, 1 mM EDTA). The final pellet was resuspended in SDS-PAGE sample buffer and analyzed by electrophoresis.

T antigen-specific monoclonal antibodies PAb416, which recognizes an epitope between amino acids 83–121, and pAb419 and PAb108, which recognize epitopes within the first 82 amino acids, and KT3, which is specific for the carboxy-terminal 11 amino acids, have been described by Harlow et al. (1981), *J. Virol.* 39:861 and Walter et al., (1980), *Proc. Nat'l. Acad. Sci. USA* 77:5197. F5, a monoclonal antibody specific for the murine polyomavirus T antigens was kindly provided by Dr. Carol Prives. Monoclonal antibodies PAb421 and PAb240, and a polyclonal antiserum (Chemicon) were used to detect p53. Antibodies IF8 (anti-pRb) and SD9 (anti-p107) were purchased from Santa Cruz Biotech. A goat anti-rabbit IgG-HRP (Sigma), or a goat anti-mouse IgG-HRP (Sigma) were used as secondary antibodies. For western-blots, the Enhanced Chemiluminescence (ECL) protocol (Amersham) was used.

The results are presented in Table I below. In Experiment A, subconfluent dishes of cells were transfected with 10 μg of DNA in which T antigen expression was driven by the SV40 promoter. In Experiment B, subconfluent dishes of cells were transfected with 5 μg of DNA in which T antigen expression was driven by the RSV promoter. The vector dl4000 makes a short truncated T antigen (amino acids 40–708) with no known biological activity (Pipas et al. (1983) *Mol. Cell. Biol.* 3:203) and was used as a negative control. The numbers in Table I represent dense foci per dish.

TABLE I

| Mutant | Transformation Amino Acid Changes | C3H10T1/2 | REF52 |
| --- | --- | --- | --- |
| Experiment A | | | |
| WT | 1 - 708 | 78, 54, 67, 51 | 118, 153 |
| DL1135 | D1 17 - 27 | 1, 0 | 0, 0 |
| 3213 | E107K, E108K | 7, 13 | 0, 0 |
| K1 | E107K | 31, 28 | 0, 0 |
| dl4000 | dl 40 - 708 | 0, 0, 0, 0 | 0, 0 |
| Experiment B | | | |
| WT | 1 - 708 | 108, 83, 70 | 142, 98, 190 |
| TN136 | 1 - 136 | 13, 18, 11 | 0, 0, 0 |
| TN136/K1 | 1 - 136/E107K | 0, 0, 0 | 0, 0, 0 |
| TN136/3213 | 1 - E107K, E108k | 0, 0, 0 | 0, 0, 0 |
| TN136/5110 | 1 - 136/D44N | 0, 0, 0 | 0, 0, 0 |

As previously reported, wild-type T antigen transformed both cell lines with equal efficiencies (Table I). In the context of full-length T antigen, the three mutations each had a different effect on transformation. As reported by Pipas et al., (1983) *Mol. Cell. Biol.* 3:203, dl1135 did not transform REF52 cells. Furthermore, this mutant failed to transform the C3H10T1/2 line. Several G418-resistant cell lines generated from transfection with dl1135 were selected and examined for T antigen expression. Cells were metabolically labeled with $^{35}$S-methionine for two hours prior to the preparation of cellular extracts. T antigen was immunoprecipitated using antibody KT3, resolved on SDS-polyacrylamine gels and visualized by autoradiography. The dl1135 T antigen was detected in both C3H10T1/2 and REF52 cells. Pulse chase experiments and Western blot analyses demonstrated that pdl1135 was relatively unstable ($t_{1/2}$=2 hours versus 12 hours for wild-type) and accumulated to about 15% of the steady-state levels of wild-type T antigen in both cell-types.

Mutant 3213 was defective for the transformation of REF52 cells, but did transform the C3H10T1/2 line at a reduced efficiency compared to wild-type. The K1 mutant consistently gave a higher frequency of transformation on C3H10T1/2 cells than the double mutant 3213, but like 3213, failed to transform the REF52 line (Table I). When cells were examined for T antigen expression as described above but using PAb416, it was found that p3213 was expressed in both transformed C3H10T1/2 sublines as well as morphologically normal REF52 cells. In both cell lines, p3213 migrated somewhat faster than wild-type T antigen through SDS-polyacrylamide gels. As previously reported, mutant 5110 showed a somewhat reduced efficiency of transformation on both cell-types, but unlike dl1135, 5110-transformed lines that expressed the mutant T antigen could be readily isolated. All three mutant T antigens bound the cellular tumor suppressor p53.

It has been reported that dl1137, a mutant that synthesizes a truncated T antigen containing only the first 121 amino acids, transforms the C3H10T1/2 line with a frequency ranging from 10–20% of wild-type but fails to transform the REF52 line (Srinivasan et al., (1989), *J. Virol.* 63:5459). The data in Table I show that TN136 behaves similarly. The T antigen fragment encoded by TN136 is relatively stable ($t_{1/2}$~6 hours) and accumulates to high levels in both C3H10T1/2 and REF52 cells as indicated by pulse-chase and Western blot experiments. The data in Table I also show the effects of the 5110, K1 and 3213 mutations on the ability of TN136 to transform C3H10T1/2 and REF52 cells. When each of the three mutations was present in TN136, the truncated T antigen was transformation-defective (Table I) even though each protein was expressed to levels comparable to that of wild-type and pTN136. The foregoing results demonstrate that alteration of any of the three conserved sequence elements present within TN136 abolishes its ability to transform.

EXAMPLE 3

Determination of Ability of J-Domain Mutants to Complement for Transformation

There is strong evidence that the transforming activities intrinsic to the J-homology region, cr2 motif, and p53-binding regions are distinct, independent T antigen functions, yet mutations in any one of these three regions render T antigen unable to transform the REF52 cell line, and reduce the transformation efficiency of C3H10T1/2 cells (Srinivasan et al. (1989); Zhu et al. (1992) *J. Virol.* 66:2780). Therefore, an investigation of the ability of mutants defective in each of these activities to cooperate in trans to transform these lines was undertaken. The results are shown in Table II.

In Experiment A, 2 µg of plasmids containing a neomycin-resistance gene (Neo) and expressing wild-type or mutant T antigens driven by the RSV promoter, and a second plasmid containing a hygromycin-resistance (Hyg) gene alone, or the Hyg gene in combination with dl1135, were cotransfected into REF52 or C3H10T1/2 cells. Colonies resistant to both Neo and Hyg were scored as having a normal flat or transformed morphology.

In Experiment B, two REF52 sublines that stably express p3213 were transfected with 5 µg of the indicated plasmids. Expression of T antigen was driven by the RSV promoter. The transfected cells were maintained in drug-free medium, and the number of transformed foci scored at three weeks.

In Experiment C, a hygromycin-resistant REF52 subline stably expressing pd11135 was transfected with 2 µg of the indicated plasmids. Colonies were selected for G418 resistance and scored as having a flat or transformed morphology.

In Experiment D, C3H10T1/2 cells expressing pd11135 were transfected with 2 µg of a plasmid expressing the indicated mutant driven by the RSV promoter, and a G418-resistance marker driven by the SV40 promoter. Following G418 selection, colonies were scored as having a normal flat, or a dense transformed morphology.

TABLE II

Complementation Assays for Cellular Transformation

Experiment A

| DNA 1 | DNA 2 | (Transformed/Flat) | | | |
|---|---|---|---|---|---|
| (Neo) | (Hyg) | REF52 | | C3H10T1/2 | |
| WT | pHyg | 67/78 | 42/27 | 56/41 | 34/28 |
| dl1135 | pHyg | 0/16 | 0/29 | 0/63 | 0/60 |
| TN136 | Phyg | 0/21 | 0/30 | 8/75 | 7/81 |
| 3213 | pHyg | 0/37 | 0/26 | 4/77 | 4/61 |
| TN136 | dl1135 | 3/48 | 1/53 | 11/68 | 13/60 |
| 3213 | dl1135 | 0/25 | 0/21 | 6/70 | 4/69 |
| pNeo | pHyg | 0/18 | 0/21 | 0/55 | 0/60 |

Experiment B

| | Transformed Foci | |
|---|---|---|
| Mutant | REF3213-1 | REF3213-2 |
| WT | 103,116 | 168,120 |
| dl1135 | 0,0 | 0,0 |

TABLE II-continued

Complementation Assays for Cellular Transformation

| TN136 | 0,0 | 0,0 |
|---|---|---|
| Mock | 0,0 | 0,0 |

Experiment C

| | REF1135-1 | |
|---|---|---|
| | (Transformed/Flat) | |
| WT | 29/38 | 49/32 |
| TN136 | 0/29 | 0/38 |
| TN136/3213 | 0/36 | 0/23 |
| dl1135 | 0/30 | 0/31 |
| 3213 | 0/32 | 0/35 |
| RSV-neo | 0/21 | 0/23 |

Experiment D

| | | Transformed/Flat | |
|---|---|---|---|
| WT | 1-708 | 68/41 | 53/59 |
| TN136 | 1-136 | 12/99 | 8/68 |
| TN136/K1 | 1-136/E107K | 0/145 | 0/131 |
| TN136/3213 | 1-136/E107K,E108K | 0/126 | 0/111 |
| dl1135 | dl 17-27 | 0/136 | 0/81 |
| 3213 | E107K,E108K | 6/85 | 10/63 |
| RSV-neo | | 0/76 | 0/88 |

As shown in Table II, TN136 failed to complement either dl1135 or 3213, and 3213 was unable to complement dl1135. Immunoprecipitation of $^{35}$S-methionine-labeled extracts of transfected cells preselected by G418-resistance showed that all the expected mutant proteins were expressed. Some transformed colonies did appear on dishes cotransfected with TN136 and dl1135, suggesting a low level of complementation. However, upon further examination it was found that all of these clones contained wild-type T antigen as evidenced by reactivity with monoclonal antibody PAb108. It was thus concluded that the wild-type T antigen in these lines was generated by recombination between dl1135 and TN136.

The failure to complement mutant versions of T antigen in trans indicates that the amino-terminal transforming functions of T antigen must exist in cis (on the same T antigen molecule) with one or more transforming activities intrinsic to the carboxy-terminal half of T antigen in order to achieve full transforming potential.

EXAMPLE 4

Effect of TN136 Expression on p53 Stability and Levels

The E1A transforming proteins of the human adenoviruses are similar in many respects to the amino-terminal transforming region of T antigen. One consequence of E1A expression is the stabilization, and increased steady-state levels of the cellular tumor suppressor p53, that results in p53-dependent apoptosis (Debbas and White, (1993), *Genes Dev.* 1:546; Laue et al. (1993) *Genes Dev.* 1:535). Although an increase in apoptosis in either CEH10T1/2 cells or REF52 cells expressing pd11137 or pTN136 was not observed, p53 stability and levels in these cells was examined.

The stability of p53 in normal C3H10T1/2 cells, d11137-transformed C3H10T1/2 cells, and CH3H10T1/2 cells expressing the adenovirus E1A region was determined as follows. Cells were labelled with $^{35}$S-methionine for one hour, chased in medium containing an excess of unlabeled methionine, and extracts were prepared as described above. The samples were then immunoprecipitated with PAb421, resolved by SDS-PAGE and the gels were scanned using an AMBIS radioanalytic imaging system. Steady-state levels of p53 in CH3H10T1/2 cells expressing pTN136 were determined as follows. Lysates containing 1 mg of total cellular protein were immunoprecipitated with a rabbit anti-p53 polycolonal serum, blotted onto polyvinylidenedifluoride (PVDF) membranes and probed with a monoclonal antibody cocktail containing PAb42 1, PAb246 and PAb240.

It was found that the half-life of p53 in the C3H10T1/2 cell line, and in sublines expressing d11137, was about 20 minutes. Similar results were obtained in sublines expressing pTN136. Consistent with these findings, an immunoblot analysis revealed no increase in the steady state levels of p53 in pTN136-expressing lines. On the other hand, expression of the E1A 243R protein in CH3H10T1/2 cells did lead to increased p53 stability ($t_{1/2}$~1.2 H) and steady-state levels, indicating that the normal p53 response pathway was functional in this cell line. Similar results were obtained in the REF52 cell line.

EXAMPLE 5

Effect of 3213 and K1 Mutations on the Phosphorylation State of TN136

It was noted while conducting the experiments in the previous examples that TN136 protein migrated to multiple bands when electrophoresed through SDS-polyacrylamide gels. When TN136 was expressed using a baculovirus vector system, multiple bands were also evident. In contrast, when the 3213 or K1 mutations were placed within TN136, the proteins were apparent as a single band with a faster mobility than the TN136 protein. To assess the amount of phosphate in these proteins, cells were metabolically labeled with 500 $\mu$Ci/ml [$^{32}$P]-orthophosphate for two hours, and cell extracts were prepared. Cell extracts were immunoprecipitated with PAb416 and analyzed by SDS-polyacrylamide gel electrophoresis (SDS-PAGE) and fluorography. The results demonstrated that the TN136/3213 protein is under phosphorylated relative to the TN136 protein, although both contain a significant amount of phosphate.

This result was confirmed by experiments in which the TN136 protein and its 3213 derivative were treated with phosphatase before electrophoresis. C3H10T1/2 cells expressing TN136 or TN136/3213 were metabolically labeled with $^{35}$S-methionine, and extracts were prepared and immunoprecipitated with Pab416. The immunoprecipitates were recovered using Protein-A Sepharose beads and washed as described in Example 2. The Sepharose beads were finally washed in potato acid-phosphatase (PAP) buffer and then treated with PAP. Control reactions were identical except that phosphatase inhibitors were added along with PAP. After treatment, the beads were washed again and analyzed by SDS-PAGE. PAb102, which recognizes an epitope in the carboxy-terminus of T antigen that is not present in TN136, was used as a negative control in the immunoprecipitations.

Treatment of the TN136 protein isolated from either transformed C3H10T1/2 cells or from bacoluvirus-infected insect cells expressing TN136 with PAP resulted in the conversion of TN136 to a single rapidly migrating band. Phosphatase treatment had no effect on the migration of the TN136/3213 protein.

It can be concluded from the foregoing results that the 3213 mutation results in a hyperphosphorylation of the TN136 protein. Similar results were obtained for the K1 mutation, indicating that the K1 mutation has a similar effect on TN136 phosphorylation.

EXAMPLE 6

Interaction of T antigen mutants with pRB, p107 and p130

The intrinsic ability of the T antigen mutants 3213, d11135, 5110, TN136, TN136/3213 and TN136/K1 to associate with members of the retinoblastoma family of tumor suppressors was examined. Sf9 cells were coinfected with baculoviruses expressing each T antigen and pRb, p107 or p130. Baculovirus producing human pRb was provided by Dr. Robert Weinberg of the Massachusetts Institute of Technology, and the baculovirus expressing p107 was provided by Dr. Dan Peeper of the Dana Farber Cancer Institute. The recombinant baculovirus expressing p130 from amino acid 372 to the carboxy-terminus was generated by inserting an ATG codon upstream of codon 372 of a p130 cDNA followed by standard procedures for baculovirus production.

Lysates were prepared from the infected cells about 43 hours post infection as described above. Approximately 100 $\mu$g of each bacoluvirus lysate (1 mg for the d11135 lysate) was incubated with 1 $\mu$g of PAb416 for 45 minutes at 4° C. to immunoprecipitate T antigen and associated proteins. For a positive control, extracts were also immunoprecipitated using pRb, p107 or p130 antibodies as appropriate. Pellets were then washed three times with SNNTE (5% sucrose, 1% NP-40, 0.5M NaCl, 50 mM Tris pH 7.5, and 5 mM EDTA), once with NTE (50 mM NaCl, 1 mM Tris pH 7.5, and 1 mM EDTA), resuspended in 15 $\mu$l sample buffer and resolved by 13% SDS-PAGE. The separated proteins were then transferred to PVDF membranes and blocked in 1× phosphate buffered saline (PBS) plus 10% nonfat dried milk for 30 minutes. The Rb-family member present in complex with T antigen was detected by immunoblotting with IF8 (anti-RB, Santa Cruz Biotech), SD9 (rabbit polyclonal p107 antibody, Santa Cruz Biotech) or an anti-p130 rabbit anti-peptide antibody. The blots were washed three times for ten minutes each in rinse buffer (blotting buffer plus 0.1% Tween-20). The blots were probed with a horseradish peroxidase (HRP) conjugated goat anti-rabbit antibody for one hour, washed as above, and the pRb, p107 or p130 was detected by ECL (Amersham).

Immunoblotting indicated that the TN136 protein bound pRb as well as or better than wild-type T antigen. Mutant 3213 failed to associate with pRb while the d11135 and 5110 mutations did not affect T antigen interaction with pRb. Both fill length wild-type T antigen and TN136 protein also associate with p107 and p130. However, in this case the 3213 mutation reduced, but did not eliminate, the association of the protein with p107 and p130. A significant amount of p107 and p130 remained complexed to the 3213 protein. In contrast, when the K1 mutation was placed in the context of the TN136 protein, the association with p107 and p130 was completely eliminated. From these results it can be concluded that the interaction of p107 and p130 with the cr2 motif is influenced by amino acids within the carboxy-terminal two-thirds of T antigen.

EXAMPLE 7

Effect of TN136 Protein on hsc70 ATPase Activity

The effects of full-length wild type T antigen and the TN136 protein on the ATPase activity of mammalian hsc70 were tested as follows.

Mammalian hsc70 was obtained from StressGen, Inc., 4243 Glanford Ave., Victoria, British Columbia, Canada. ATPase assays were performed as described by Cyr et al. (1992) *J. Biol. Chem.* 267:20927 and contained 30 pm hsc70, 10 $\mu$M ATP, about 2 $\mu$Ci of $\alpha$-[$^{32}$P]-ATP (Amersham), and 15 pm of wild-type T antigen or 60 pm of TN136 protein. The reaction mixtures were incubated at 37° C., and aliquots were removed at 10, 20, 30 and 40 minutes and spotted onto cellulose PEI thin layer chromatography plates (Fisher Scientific) and developed in 0.5M LiCl/1M formic acid. ATPase activity was apparent by the amount of $\alpha$-[$^{32}$P]-ADP liberated during the reaction. The amount of ATP hydrolyzed was determined by a radio analytical imaging system (AMBIS Systems, San Diego, Calif.). Results were obtained on a Fuji phosphoimager and quantified using the MacBas software program (version 2.2) from Fuji Photo Film Inc.

Figure 2A:
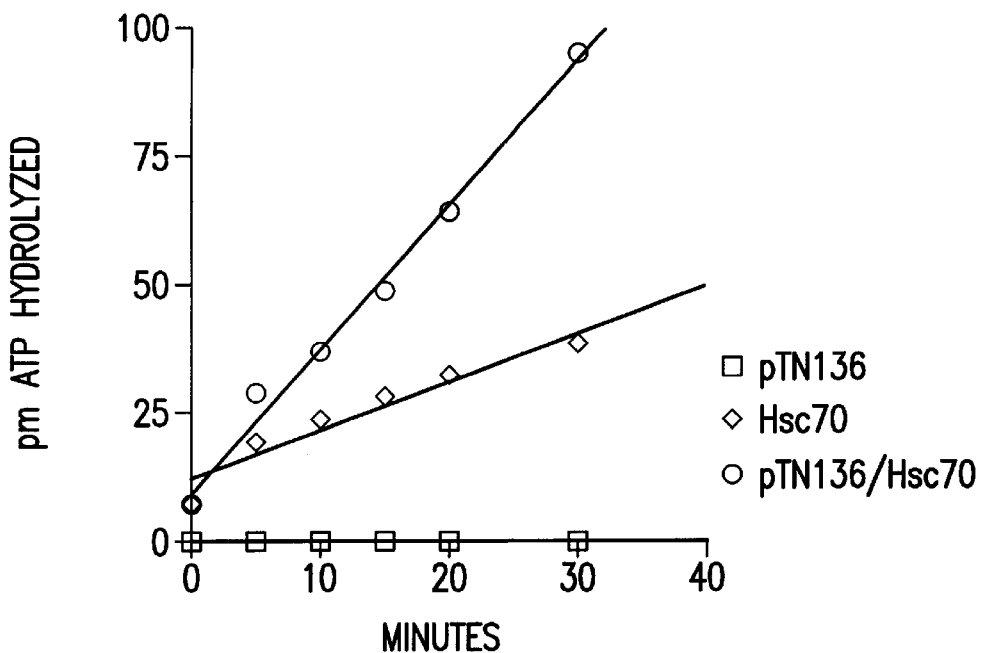
FIGS. 2A–2C provide graphs of the amount of ATP hydrolyzed in ATPase assays containing hsc70 and wild-type T antigen or TN136.
Figure 2B:
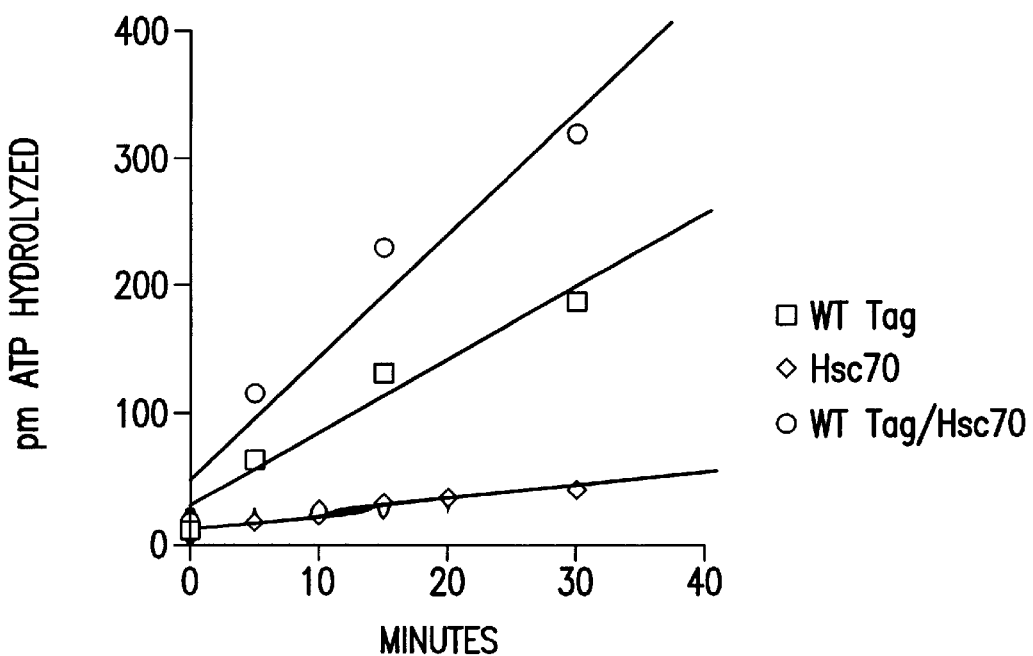

As shown in FIG. 2A, the addition of TN136 protein resulted in a five-fold increase in the ATPase activity of hsc70. FIG. 2B shows that full length T antigen also activated the hsc70 ATPase. Full length wild-type T antigen had a higher rate of ATP hydrolysis (8.2 pm ATP hydrolyzed per minute) than hsc (2.2 pm/min), while the combination of the two showed a synergistic effect (14.5 pm/min).

Figure 2C:
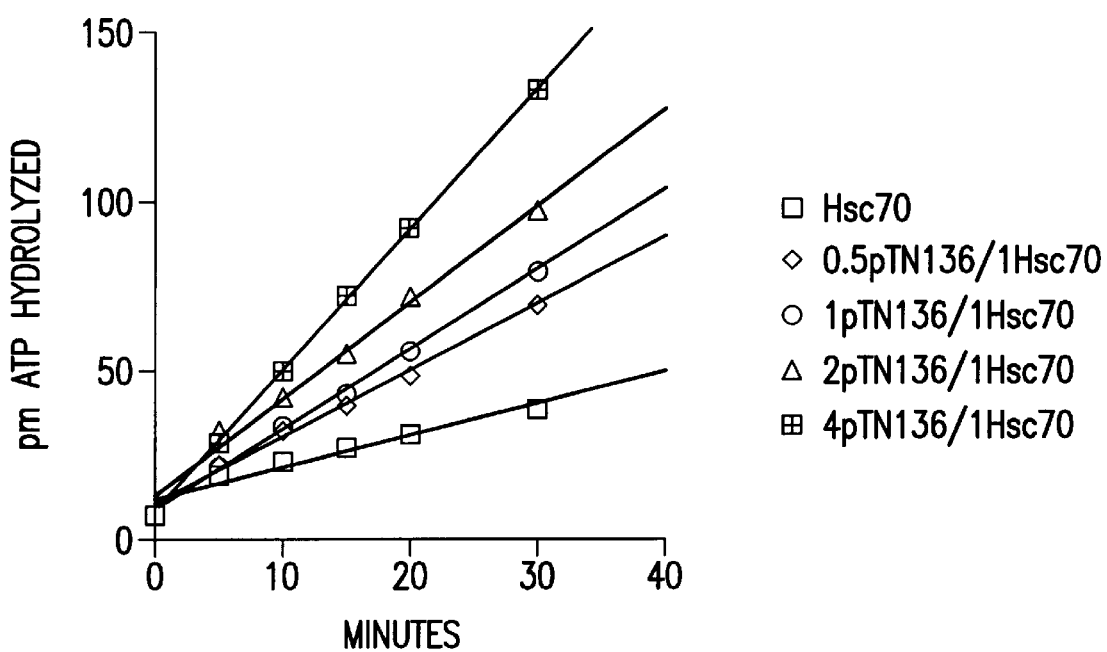

The effect of increasing levels of TN136 protein was determined by performing the reaction with varying amounts of TN136 protein from 15 pm to 120 pm. As shown in FIG. 2C, the level of activation of hsc70 ATPase increased with increasing levels of TN136.

A variety of irrelevant proteins, including bovine serum albumin and a monoclonal antibody, each failed to activate the hsc70 ATPase.

EXAMPLE 8

Effect of TN136 Protein on the ATPase Activity of Ssa1p

The ATPase activity of Ssa1p, a yeast cytosolic hsc70 homologue, is elevated 8–10-fold by its DnaJ partner Ydj1p, while peptides stimulate Ssa1p's ATPase activity 2-fold or less (Cyr et. al. (1992) *J. Biol. Chem.* 267:20927; Ziegelhoffer et al. (1995) *J. Biol. Chem.* 270:10412). Ydj1p and ATP are also able to promote the release of a permanently unfolded protein, carboxymethyl lactalbumin (CMLA) from Ssa1p in vitro (Cyr et al. (1992)).

The ability of T antigen to activate the ATPase activity of Ssa1p was assayed as follows. Ssa1p was purified as described by Brodsky et al. (1993) *J. Cell Biol.* 120:95 and dialyzed against buffer containing 50 mM Tris-HCl, pH 7.4, 50 mM NaCl, 2 mM MgOAc, 0.8 mM DTT and 5% glycerol. Ydjp1 was purified as described by Cyr et al. (1992). ATPase assays were performed as described by Cyr et al. (1992) and contained 1 $\mu$g of Ssa1p, 1 $\mu$g TN136 protein or Ydj1p, 50 $\mu$M ATP, and about 2 $\mu$Ci of $\alpha$-[$^{32}$P]-ATP. ATPase assays were also conducted in the absence of Ssa1p and the indicated proteins. ATPase activity was determined as described in Example 7.

Figure 3:
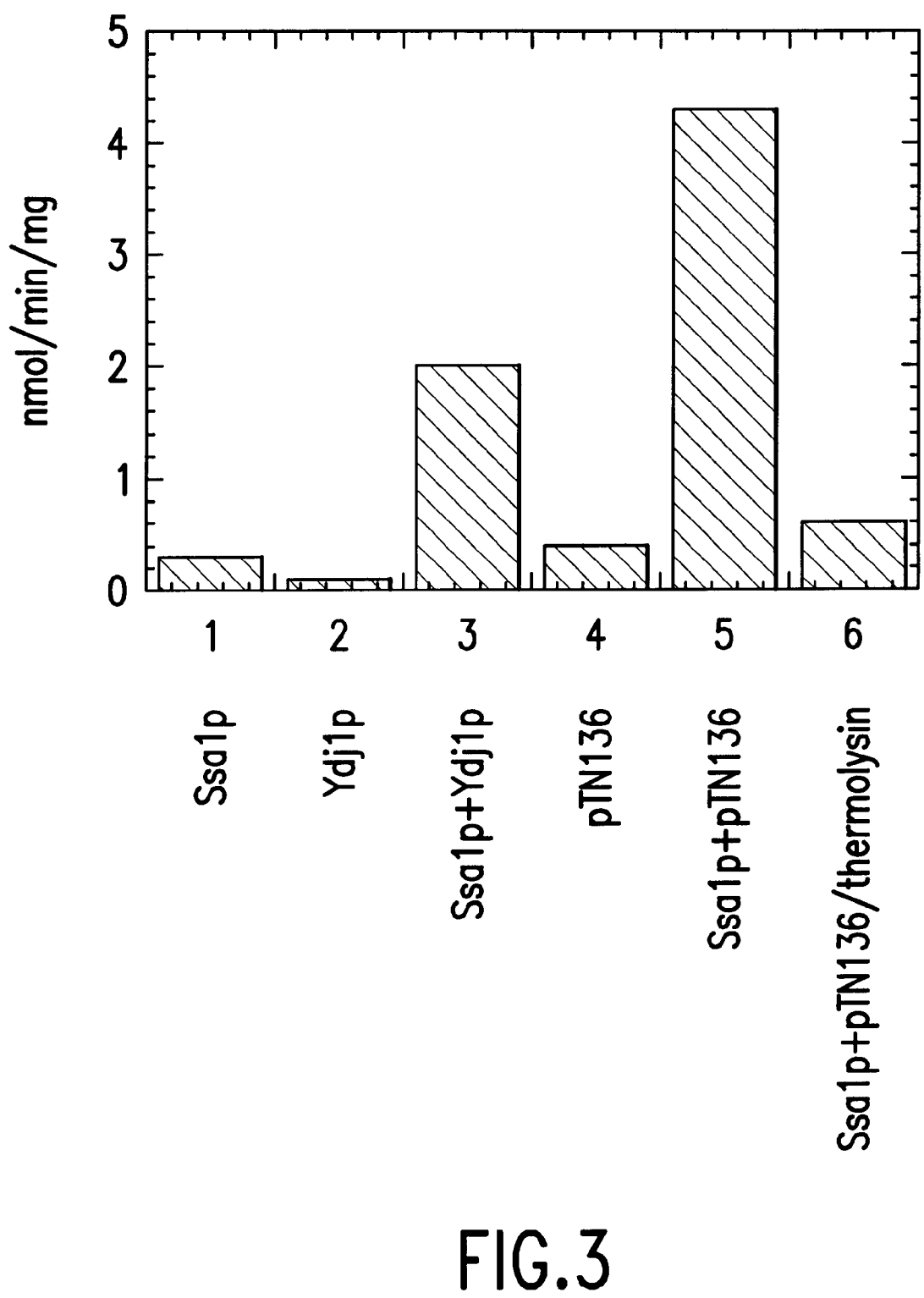
FIG. 3 is a graph demonstrating the ATPase activity of Ssa1p in the absence and presence of Ydj1p or TN136 proteins.

As shown in FIG. 3, TN136 protein activated the ATPase activity of Ssa1p 9.4-fold. Treatment of TN136 protein with thermolysin, which completely hydrolyzed the protein, eliminated its ability to stimulate the ATPase activity of Ssa1p (FIG. 3). Activity is expressed in nmol ATP hydrolyzed per minute per mg of Ssa1p.

Figure 4:
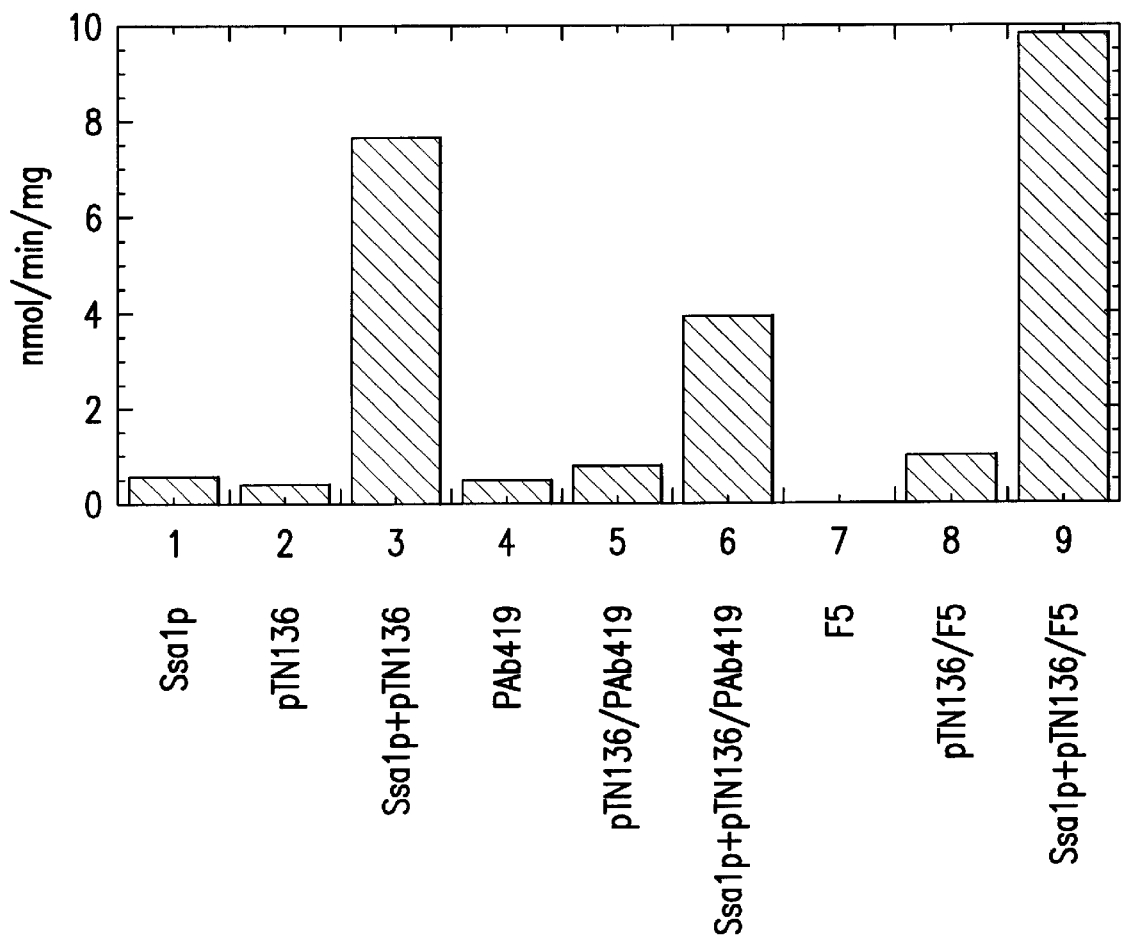
FIG. 4 is a graph demonstrating the ATPase activity of Ssa1p in the presence of TN136 protein and the absence or presence of antibody PAb419 or F5.

To determine the specificity of ATPase activation by TN136 protein, the ability of TN136 to stimulate the ATPase activity of Ssa1p was assessed in the presence of PAb419, a monoclonal antibody directed against TN136 protein. The PAb419 epitope maps near the amino-terminal 30 amino acids of T antigen, and is destroyed by the deletion present in d11135 (Clark et al. (1983) *Mol. Cell. Biol.* 3:220). A monoclonal antibody specific for the murine polyomavirus, F5, was also tested. F5 is known to react poorly with SV40 T antigen. TN136 protein was incubated with the indicated antibody for 45 minutes at about 20° C. before Ssa1p was added to the reaction. As shown in FIG. 4, PAb419 inhibited TN136-activation of Ssa1p's ATPase activity by about two-fold. F5 marginally stimulated the ATPase activity.

The ability of two ATPase-defective T antigen mutants, 5030 and 5061, to activate Ssa1p was determined. ATPase assays were performed as described above and the relative ATPase activities were normalized to that of Ssa1p in the absence of any other factors. Both 5030 and 5061 stimulated the Ssa1p ATPase activity from five- to six-fold, and exhibited little endogenous ATPase activity when assayed alone.

This example demonstrates that large T antigen contains a J-domain that is able to interact functionally with Ssa1p.

EXAMPLE 9

Ability of T Antigen to Promote the Release of an Unfolded Protein from Ssa1p

Figure 5:
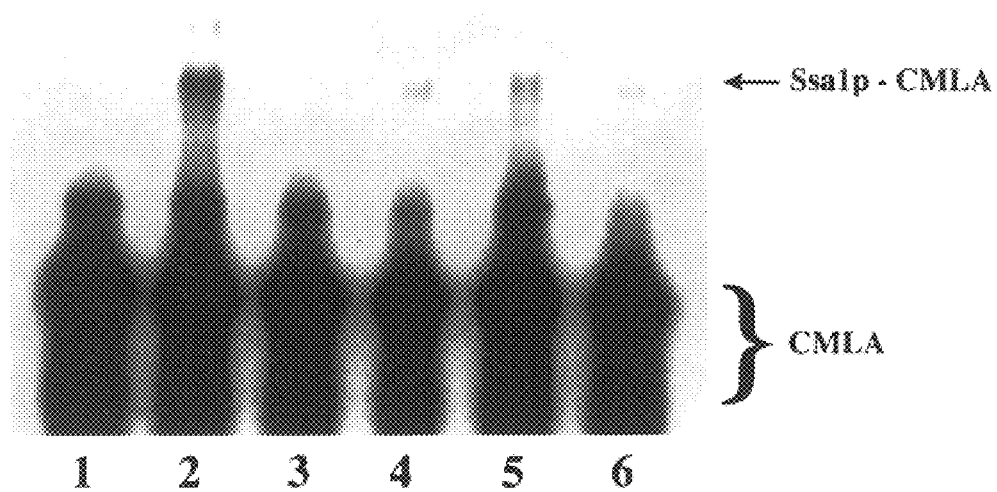
FIG. 5 is an autoradiograph depicting the release of CMLA from Ssa1p in the presence of a J-domain.

The ability of T antigen to promote the release of an unfolded protein from Ssa1p was determined as follows. Carboxymethyl lactalbumin (CMLA, Sigma) was iodinated and incubated with Ssa1p and Ydj1p, T antigen, 5030, or TN136 protein in the presence of ATP as described by Cyr et al. (1992). All reactions contained 1 mM ATP in an ATP regenerating system as described by Brodsky et al. (1993). Ssa1p-CMLA complexes were resolved by running 7.5–15% native polyacrylamide gels supplemented with 1 mM ATP at 4° C. overnight. FIG. 5 depicts the results for reactions containing radioiodinated CMLA either alone (lane 1) or in the presence of 0.6 $\mu$M Ssa1p (lane 2), and 2.6 $\mu$M Ydj1p (lane 3), 1.28 $\mu$M T antigen (lane 4), 2.6 AM p5030 (lane 5), and 5.2 $\mu$M TN136 (lane 6). As demonstrated therein, Ydj1p promotes the release of CMLA from Ssa1p in the presence of ATP (FIG. 5, lane 3). T antigen was also able to effect this release (FIG. 5, lane 4), as was the ATPase defective variant, 5030 (FIG. 5, lane 5), and the T antigen J-domain, TN136 (FIG. 5, lane 6). T antigen and Ydj1p-mediated release occurred at nearly identical levels in these assays.

From the foregoing results, it can be concluded that the J-domain of T antigen acts in vitro as a DnaJ-like chaperone for the yeast DnaK chaperone, Ssa1p. The SV40 T antigen may utilize a chaperone mechanism for infection by directing the association of hsc70, or another DnaK-family chaperone, to multiprotein complexes that are targets for T antigen action.

EXAMPLE 10

Identification of Agents that Block Stimulation of Ssa1p ATPase by TN136

Purified Ssa1p (1 $\mu$g) was mixed with a four-fold molar excess of immunoaffinity purified TN136 protein (1 $\mu$g) or TN136-5110 (1 $\mu$g) and $\alpha$-[$^{32}$P]-ATP in a buffer containing 1 nmole cold ATP (50 $\mu$M) in a total volume of 20 $\mu$L. Reactions were incubated at 30° C. for either 30 or 60 minutes. Reactions were carried out in triplicate. Hydrolysis of the $\alpha$ phosphate of ATP was monitored by the appearance of $\alpha$-[$^{32}$P]-ADP, a species that migrates apart from ATP on silica gel thin layer chromatograms. The ATPase activity, determined by quantifying the amount of liberated α-[$^{32}$P]-ADP, was obtained by phosphoimage analysis of the resulting chromatogram.

To test the ability of agents to block the stimulation of the ATPase activity of Ssa1p by TN136, identical assays were performed except that the candidate agent was preincubated with TN136 for 45 minutes at room temperature with occasional mixing prior to the addition of Ssa1p and α-[$^{32}$P]-ATP. Candidate agents tested were PAb416 (5 µg) and PAb419 (5 µg) and antibody F5 (5 µg).

The following specific activities (nmoles converted to ADP/min/mg Ssa1p) were observed:

TABLE III

| Ssa | Ssa1p + N136 | Ssa1p + N136 + 416 | Ssa1p + N136 + 419 |
| --- | --- | --- | --- |
| .63 | 6.56 | 4.78 | 3.44 |

The results in Table III indicate that TN136 stimulated the ATPase activity of Ssa1p approximately 9.4-fold. The 416 antibody, which is specific for the amino-terminus of T antigen, resulted in a 1.4-fold inhibition of N136 stimulation. The 419 antibody, also specific for the amino-terminus of T antigen, resulted in a greater than 2-fold inhibition of TN136 stimulation. Antibody F5, which recognizes murine polyoma virus, had no detectable effect. None of the antibodies has the ability to stimulate Ssa1p nor do they have inherent ATPase activity.

Figure 6:
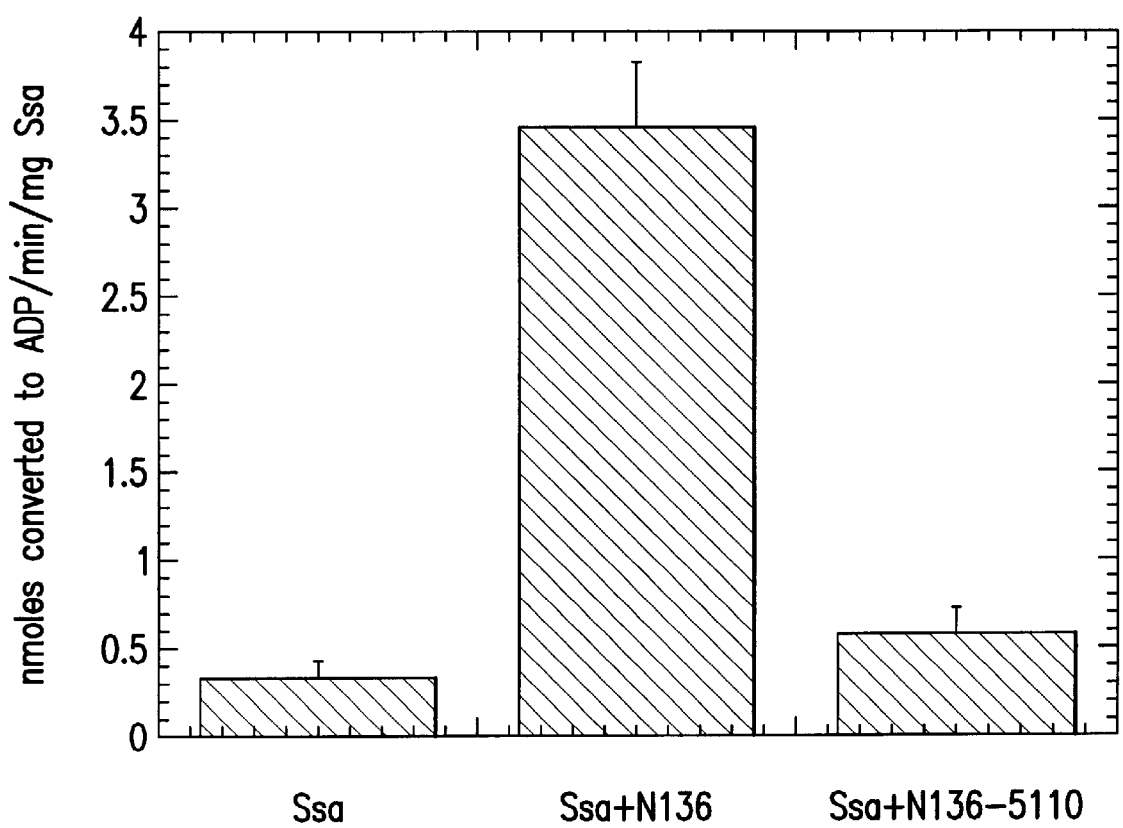
FIG. 6 is a graph of the ATPase activity of Ssa1p alone and stimulated by TN136 and TN136-5110.

The results of another assay are shown in FIG. 6. As demonstrated therein, TN136 stimulated the Ssa1p ATPase activity about 10-fold. The transformation-defective mutant of N136, N136-5110, did not stimulate the Ssa1p ATPase. Similar results were obtained with other transformation-defective mutants of N136.

Similar assays were performed to test the ability of the full length T antigen and the 5030 and 5061 T antigen mutants to stimulate the ATPase activity of Ssa1p. Full length T antigen stimulated Ssa1p approximately 5.2-fold after the inherent ATPase activity of T antigen was subtracted. The 5030 T antigen mutant stimulated Ssa1p approximately 6-fold and had no residual activity alone. The 5061 T antigen mutant stimulated Ssa1p approximately 5.4-fold and had no residual ATPase activity.

EXAMPLE 11

J-domain of T Antigen Rescues ydj1-151 Defect

The *S. cerevisiae* mutant ydj1-151 (Caplan et al. (1992) Cell 71:1143–1155) is a temperature-sensitive mutant that fails to grow at temperatures at or above 35° C. due to a mutation that renders the cytosolic DnaJ protein, Ydj1p, defective. To determine whether the J-domain of T antigen can rescue this defect, a hybrid protein was engineered in which the J-domain of Ydj1p was replaced by the J-domain of the SV40 T antigen. The hybrid protein, designated T-Ydj1p, was created by inserting the fusion protein containing amino acids 1–82 of T antigen into Ydj1p such that the first 70 amino acids of Ydj1p were replaced with the T antigen (1–82) fragment. The cloning was achieved by two rounds of PCR. The first round inserted an EcoR1 site in the DNA encoding the N terminus of the T antigen DnaJ domain and a Not1 site in the DNA encoding the C terminus of Ydj1, as well as complementing regions at the junction of the DnaJ domains and the rest of the proteins. The products were annealed and a second round of PCR using the N and C end DNA primers was used to obtain full length genes encoding the fusion proteins. The genes were placed into the pYes2 expression vector from Stratagene at the EcoR1 and Not1 sites and transformed into the ydy1-151 strain using lithium acetate-mediated transformation (Rose et al., 1990). Cells were grown on selective medium (Sc-ura) containing 2% glucose to select for transformants, and to express the fusion protein, were re-plated onto Sc-ura medium containing 2% galactose. Cells were grown at the permissive temperature for ydj1 mutant cells (26° C.) unless the ability of the fusion protein to rescue the ydj1 mutations was assayed, in which case the plates were incubated at 26° C., 30° C., 35° C., and 37° C.

Ydj1p mutant yeast were transformed with vectors containing DNA encoding the hybrid protein, T-Ydj1p, under conditions whereby expression was induced only in the presence of galactose. T-Ydj1p was made as described above. The transformed mutant yeast survived at 25° C. in the presence of glucose, grew poorly at 35° C., and failed to grow at 37° C. In the presence of galactose, the transfected mutant yeast were able to grow well at 25° C. and 35° C. and grew somewhat at 37° C. These results demonstrate that T-Ydj1p rescued the ydj1-151 defect and allowed growth at the elevated temperature.

These results were confirmed by engineering altered forms of T-Ydj1p in which a histidine (amino acid 42) and aspartic acid (amino acid 44), that are conserved in all DnaJ chaperones, were mutated. Ydj1p cells transformed by DNA encoding the altered T-Ydj1p and grown in galactose exhibited almost no growth at 37° C. and poor growth at 35° C. These results indicated that the mutated J-domain in the T antigen was not fully functional.

We claim:

1. A method of identifying an agent that interferes with the interaction of a J-domain and a DnaK protein comprising:

contacting a polypeptide comprising the J-domain of SV40 T antigen with a DnaK protein in the presence of ATP and in the absence of an agent to be tested for its ability to block the stimulation of ATPase activity;

determining the stimulation of ATPase activity of the DnaK protein by the polypeptide comprising the J-domain of SV40 T antigen;

contacting a polypeptide comprising the J-domain of SV40 T antigen with the DnaK protein in the presence of ATP and in the presence of an agent to be tested for its ability to block the stimulation of ATPase activity;

determining the stimulation of ATPase activity of the DnaK protein by the polypeptide comprising the J-domain of SV40 T antigen in the presence of the agent to be tested; and comparing the stimulation of ATPase activity in the absence and presence of the agent to be tested, wherein a decrease in ATPase activity in the presence of the agent indicates an agent that interferes with the activation of a DnaK protein by a protein comprising a J-domain.

2. The method of claim 1 wherein said polypeptide has the amino acid sequence of SEQ ID NO:1.

3. The method of claim 1 wherein said polypeptide has the amino acid sequence of SEQ ID NO:2.

4. The method of claim 1 wherein said DnaK protein is selected from the group consisting of mammalian hsc70, *E. coli* DnaK, and *S. cerevisiae* Ssa1p.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 82 amino acids
      (B) TYPE: amino acid
      (C) STRANDEDNESS: single
      (D) TOPOLOGY: linear -continued (ii) MOLECULE TYPE: None (xi) SEQUENCE DESCRIPTION: SEQ ID NO:1:

Met Asp Lys Val Leu Asn Arg Glu Glu Ser Leu Gln Leu Met Asp Leu
1               5                   10                  15

Leu Gly Leu Glu Arg Ser Ala Trp Gly Asn Ile Pro Leu Met Arg Lys
                20                  25                  30

Ala Tyr Leu Lys Lys Cys Lys Glu Phe His Pro Asp Lys Gly Gly Asp
                35                  40                  45

Glu Glu Lys Met Lys Lys Met Asn Thr Leu Tyr Lys Lys Met Glu Asp
        50                  55                  60

Gly Val Lys Tyr Ala His Gln Pro Asp Phe Gly Gly Phe Trp Asp Ala
65                  70                  75                  80

Thr Glu (2) INFORMATION FOR SEQ ID NO:2:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

Met Asp Lys Val Leu Asn Arg Glu Glu Ser Leu Gln Leu Met Asp Leu
1               5                   10                  15

Leu Gly Leu Glu Arg Ser Ala Trp Gly Asn Ile Pro Leu Met Arg Lys
                20                  25                  30

Ala Tyr Leu Lys Lys Cys Lys Glu Phe His Pro Asp Lys Gly Gly Asp
                35                  40                  45

Glu Glu Lys Met Lys Lys Met Asn Thr Leu Tyr Lys Lys Met Glu Asp
        50                  55                  60

Gly Val Lys Tyr Ala His Gln Pro Asp Phe Gly Gly Phe Trp Asp Ala
65                  70                  75                  80

Thr Glu Ile Pro Thr Tyr Gly Thr Asp Glu Trp Glu Gln Trp Trp Asn
                85                  90                  95

Ala Phe Asn Glu Glu Asn Leu Phe Cys Ser Glu Glu Met Pro Ser Ser
                100                 105                 110

Asp Asp Glu Ala Thr Ala Asp Ser Gln His Ser Thr Pro Pro Lys Lys
        115                 120                 125

Lys Arg Lys Val Glu Asp Pro Lys
        130                 135